United States Patent [19]
Smidt et al.

[11] Patent Number: 4,462,252
[45] Date of Patent: Jul. 31, 1984

[54] TRUNK DYNAMOMETER

[75] Inventors: Gary L. Smidt, Iowa City, Iowa; Louis R. Amundsen, New Brighton, Minn.; Thomas B. Herring, Iowa City, Iowa

[73] Assignee: The United States of America as represented by the Department of Health and Human Services, Washington, D.C.

[21] Appl. No.: 422,304

[22] Filed: Sep. 23, 1982

[51] Int. Cl.³ .............................................. G01L 5/02
[52] U.S. Cl. ..................................................... 73/379
[58] Field of Search ....................... 73/379–381; 128/774, 781; 272/134, DIG. 4, DIG. 5

[56] References Cited

U.S. PATENT DOCUMENTS

| 3,012,776 | 12/1961 | Hotas | 272/134 X |
| 3,285,070 | 11/1966 | McDonough | 73/379 |
| 3,374,675 | 3/1968 | Keropian | 73/379 |
| 3,465,592 | 9/1969 | Perrine | 73/379 |
| 3,752,144 | 8/1973 | Weigle, Jr. | 73/379 X |
| 3,784,194 | 1/1974 | Perrine | 272/DIG. 6 |

FOREIGN PATENT DOCUMENTS

| WO80/00308 | 3/1980 | PCT Int'l Appl. | 73/379 |
| WO80/02668 | 8/1982 | PCT Int'l Appl. | 73/379 |

OTHER PUBLICATIONS

J. A. Vos et al.–Telemetry of Biomechanical Forces During Exercise", Conference: International Symposium on Biotelemetry, Nijmeger, The Netherlands, May 1971.

*Primary Examiner*—Charles A. Ruehl
*Attorney, Agent, or Firm*—Holman & Stern

[57] ABSTRACT

A trunk dynamometer measures isometric and concentric strength and muscular endurance of the extensors and flexors of the lumbar and thoracic spine. A stabilization seat assembly immobilizes the pelvis, thighs, knees, and feet of the subject and is movable relative to a mainframe to permit the subject's axis of spinal flexion and extension to be aligned with the rotation axis of a torque transducer shaft. A laser alignment arrangement cooperates with a sacral stabilizer pad to assure proper alignment of the axes. Anterior and posterior trunk pads are adjustable in height and are linked to the torque transducer shaft to tansmit the subject's spinal flexion and extension efforts as torque to the transducer shaft. An accessory shaft, also linked to the trunk pads and aligned with the transducer shaft axis, has a counterweight rigidly suspended therefrom to compensate for torque applied to the transducer by the trunk pads alone.

18 Claims, 8 Drawing Figures

TRUNK DYNAMOMETER

BACKGROUND OF THE INVENTION

1. Technical Field

The present invention relates to a method and apparatus for measuring isometric and concentric strength and muscular endurance of a human subject's extensor and flexor muscles used in rotating the trunk of the subject.

2. Description Of The Prior Art

The generally accepted measurement criterion for the maximum tension which can be exerted by a muscle is the maximum moment of force that a muscle can exert on a body part. This is referred to as the maximum strength of the muscle and is expressed, for example, in kilograms per square centimeter of transverse section. In order to be meaningful, this measurement parameter must be expressed relative to the length of the muscle or the position of the body part. Several factors influence the validity of muscle strength tests. First, the muscle or muscle groups to be tested must be isolated from muscles which may contribute a moment to the measurement apparatus. This is accomplished by positioning the subject appropriately and stabilizing the parts of the body containing muscles which are not part of the measurement. Second, the moment or torque measuring device must be oriented perpendicular to the moment arm of the body part. The measuring device must also operate in the plane of motion of the body part. This requires a reasonable estimate of the axis of rotation of the body part involved.

Strength measurements should be taken at a proportional distance from the axis of rotation of the body part comparing measurements from different subjects. This is particularly important when the force exerted by the body part is the parameter to be measured. With respect to this methodology, moment measurements should also be taken at a proportional distance from the axis of rotation.

A widely used device for measuring strength and endurance of human muscles is the Cybex II, manufactured by Cybex, a division of Lumex, Inc., of Bay Shore, N.Y. This device is described in various catalogues produced by the manufacturer and also in U.S. Pat. No. 3,465,592 to Perrine, which patent is expressly incorporated herein by reference. In this apparatus, muscular strength and endurance is measured as a function of the torque or moment applied by muscular exertion to rotate an input shaft about its axis. The Cybex II is a passive component and does not apply force to the subject; it merely measures the torque applied to the device by the subject. A speed control unit permits the maximum rate of angular displacement of the input shaft to be set from 0° per second to 210° per second. When the speed control is set at 0° per second, the subject is able to apply torque to the input shaft but the input shaft does not rotate. This configuration is used to measure isometric strength of the muscle involved. When the speed control is set at values greater than 0° per second, the input shaft will rotate, in response to applied torque from the subject, through a range of motion at a constant velocity for as long as the subject applies torque to the system. This latter configuration is employed to measure the concentric strength and muscular endurance of the subject.

Although the Cybex II is useful in exercising trunk flexion and extension, it does not properly measure the strength and endurance of the flexors and extensors of the lumbar and thoracic spine. The reason for this is that the Cybex II does not provide two (2) critically important features which are required to accurately measure the strength and endurance of the flexors and extensors. Specifically, the Cybex II does not provide for immobilization of other muscles which a subject involuntarily employs in flexing and extending his or her trunk about the axis of rotation of spinal flexion and extension. Further, the Cybex II provides no means for accurately positioning the axis of rotation of spinal flexion and extension with respect to the axis of the torque transducer input shaft; that is, these two (2) axes must be reasonably aligned in order to have valid strength and endurance measurements.

SUMMARY OF THE INVENTION

The primary object of this invention is to provide a method and apparatus for measuring the strength and endurance of the flexors and extensors of the lumbar and thoracic spine.

It is another object of the present invention to provide an accurate measurement of the isometric and concentric strength of the muscular endurance of a subject's extensor and flexor muscles used in rotating the trunk of the subject.

It is a further object of the present invention to provide a trunk dynamometer which effectively isolates the muscles involved in trunk flexion and extension.

It is another object of the present invention to provide a trunk dynamometer which permits immobilization of muscles below the axis of rotation of spinal flexion and extension but which the subject may involuntarily employ to effect flexion and extension of the trunk.

It is still another object of the present invention to provide a trunk dynamometer which permits accurate measurement of isometric and concentric strength and muscular endurance of a patient's extensor and flexor muscles used in trunk flexion and extension and which does so accurately by accurately positioning the axis of trunk rotation with respect to the axis of rotation of the input shaft of a torque transducer.

It is a further object of the present invention to provide a trunk dynamometer which effectively adapts the Cybex II torque transducer for accurate measurement of isometric and concentric strength and muscular endurance of a subject's extensor and flexor muscles used in rotating the subject's trunk.

In accordance with the present invention, a trunk dynamometer includes a mainframe, a movable stabilization seat assembly, a rotating trunk pad assembly, and a torque transducer with associated controls. The stabilization seat immobilizes the pelvis, lower extremities, and the feet of the subject by means of a series of pads and straps. A foot pad suspended from the seat immobilizes the patient's feet. Knee and thigh pads, which are positionally adjustable, immobilize the lower and the upper legs, respectively, of the subject seated in the stabilization seat. A sacral pad is capable of both vertical and anteroposterior motion and serves to limit movement of the lower spine area while aligning the trunk flexion and extension axis with the axis of the input shaft of the torque transducer. Two (2) additional pads are provided to stabilize the position of the pelvis and act on the anterior superior iliac spines (ASIS) and are referred to herein as ASIS pads. The rotating trunk pads include a pair of spaced pads which are adjustable in height above the seat. In addition, the spacing between the pads is adjustable for the ateroposterior diameter of the subject's chest. The trunk pads are linked to the input shaft of the torque transducer so that forces applied to the trunk pads in either direction are transmitted as torque to the torque transducer input shaft. An accessory shaft, also linked to the trunk pad assembly by a torque transmission connection, has a counterweight rigidly suspended therefore which is adjusted for each subject such that the torque effects produced by the weight of the trunk pads and supporting structure are nullified in the measurement.

The trunk dynamometer provides isometric and concentric strength measurements of muscles which flex and extend the human spine. Isometric strength is measured while the trunk is held stationary. Concentric strength is measured while the subject flexes or extends his or her spine. After the subject is correctly positioned in the stabilization seat, the subject is asked to maintain maximal inspiration while the trunk pads are adjusted to the chest anteroposterior diameter. The torque transducer, which is a Cybex II of the type described above, is then adjusted for the desired maximum rate of angular displacement. The subject then attempts to flex or extend his or her trunk and the applied torque is measured as a function of muscle strength.

BRIEF DESCRIPTION OF THE DRAWINGS

The above and still further objects, features, and advantages of the present invention will become apparent upon consideration of the following detailed description of one specific embodiment thereof, especially when taken in conjunction with the accompanying drawings, wherein:

FIG. 8 is a free body diagram of the pelvis of a subject positioned in the stabilization seat wherein arrows are employed to represent reaction forces applied to the subject's pelvis.

DESCRIPTION OF THE PREFERRED EMBODIMENTS

Figure 1:
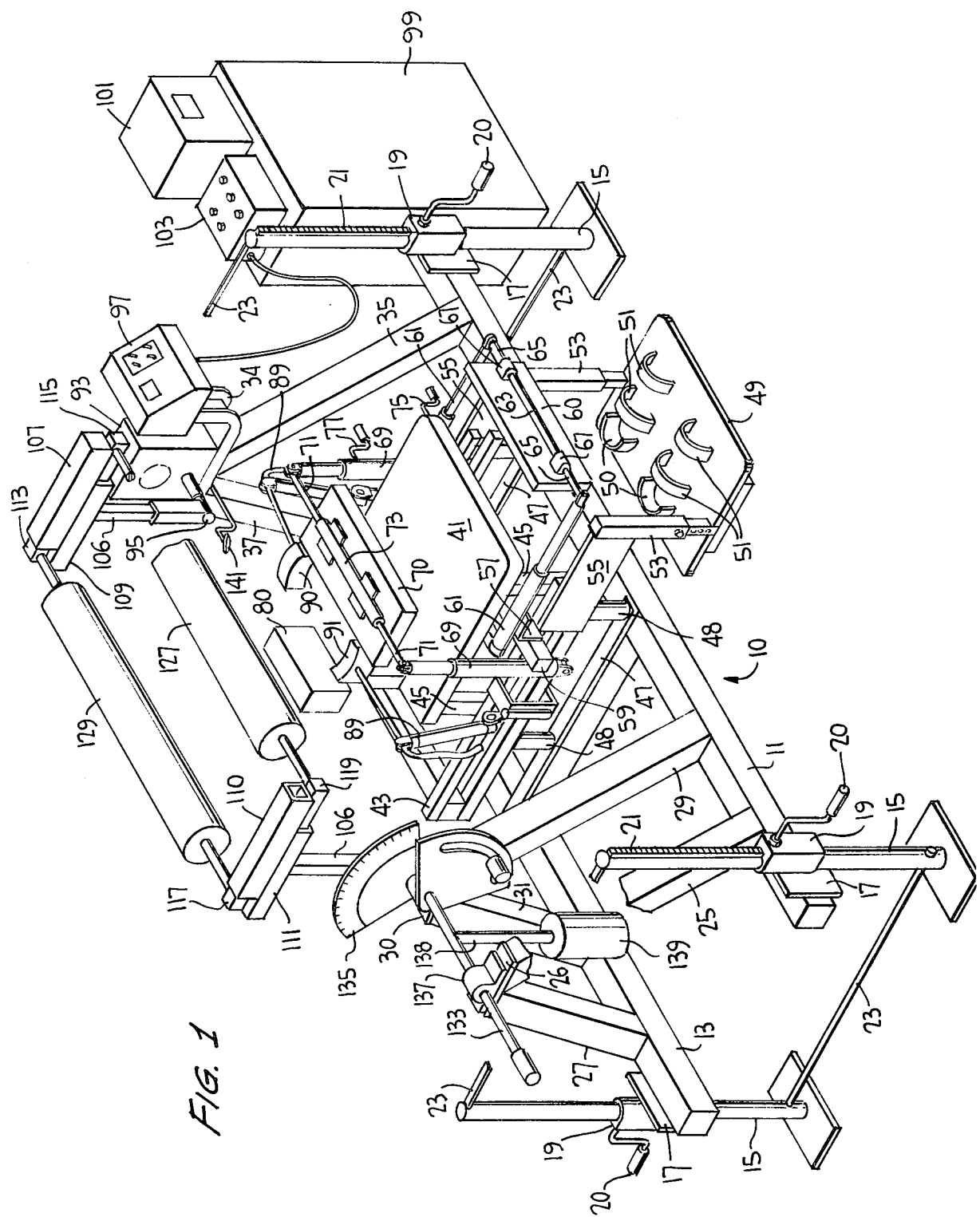
FIG. 1 is a view in perspective from the front and right side of the trunk dynamometer of the present invention wherein certain portions of the dynamometer are broken away and others are omitted for purposes of clarity of illustration.
Figure 2:
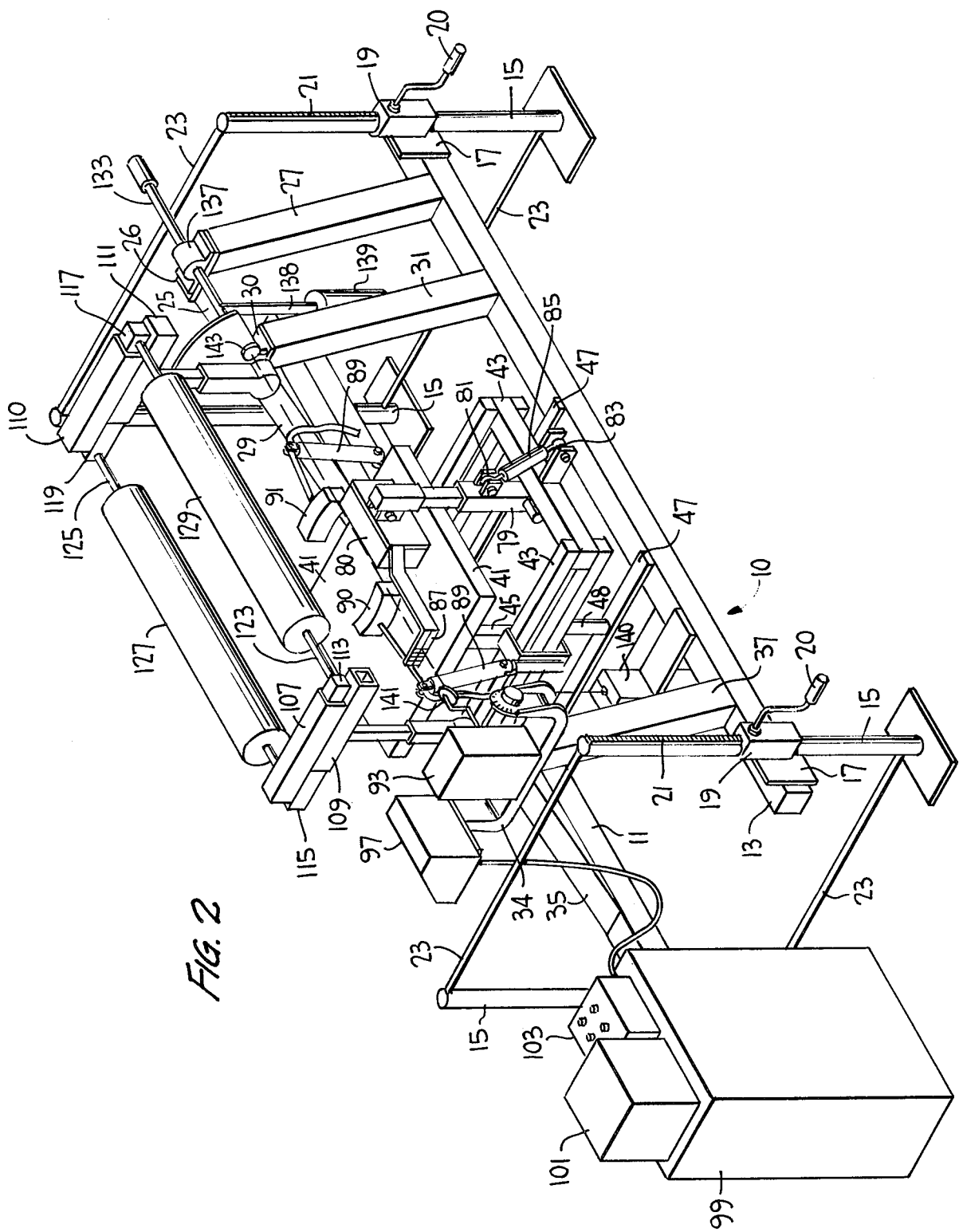
FIG. 2 is a view in perspective from the rear of the trunk dynamometer of FIG. 1 wherein certain portions of the trunk dynamometer are eliminated for purposes of clarity of illustration.

Referring specifically to FIGS. 1 and 2 of the accompanying drawings, the trunk dynamometer of the present invention is made up of a stabilization seat, a trunk pad assembly and a moment transducer, all of which are attached to a common mainframe 10. The mainframe and supporting structures of the Iowa Trunk Dynamometer are made of heavy walled tubular steel. The mainframe includes an anterior horizontal support beam 11 which is parallel to and spaced from a posterior horiztonal support beam 13. The support beams 11 and 13 are suspended above the ground at their ends by respective jack assemblies 15, each of which includes a support plate secured to a respective beam end and to a carriage 19 which rides up and down a vertically-extending rack 21 under the control of a hand crank 20. Each jack 15 controls the height at a respective end of a respective beam 11, 13. Jacks at corresponding ends of beams 11 and 13 are spaced from one another by spacer rods 23 extending from the tops and bottoms of the jacks to fix the spacing between beams 11 and 13.

The mainframe further includes an outboard truss disposed on the right-hand side (from a seated subject's perspective) of the mainframe and including beams 25 and 27 projecting upwardly in a converging manner from respective support beams 11 and 13. A top plate 26 rests atop both beams 25 and 27 and serves as the top of the outboard truss. An inboard truss on the right-hand side is generally similar to the outboard truss and includes beams 29 and 27 projecting upwardly in a converging manner from respective support beams 11 and 13. A top plate 30 serves as the top of the inboard truss on the right-hand side and is substantially coplanar with the plate 26. A further truss on the left-hand side includes beams 35 and 37 which project upwardly in a converging manner from respective support beams 11 and 13. A bracket member 34 serves as the top of the left-hand truss to support the torque transducer in the manner described hereinbelow.

As noted above, the frame and supporting structures of the trunk dynamometer are made of heavy walled tubular steel. Connections between the various tubular members are generally bolted together; however, critical connections are welded, as necessary. All of the wiring (not illustrated) exists in external harnesses and connections are made in the metallic enclosures. Except for the torque transducer, the electrical components of the trunk dynamometer are operated from the control box 97.

The stabilization seat assembly includes a padded plywood sitting platform or seat 41 supported above a tubular steel support frame 43 by means of four (4) seat support legs 45. The stabilization seat assembly is bolted to a conventional automotive power seat mechanism 150 (shown schematically in FIG. 6) of which cross-beam supports 47 form a part. The stabilization seat frame 43 moves up and down with respect to the cross-beam members 47 by sliding vertically with respect to legs 48.

A foot platform 49 has a flat top surface above which is disposed a pair of heel restraining cups 50 and a plurality of foot restraining straps 51 which are adjustable by means of Velcro fasteners. The foot platform 49 is suspended from the seat assembly frame 43 by means of a pair of adjustable support members 53 and respective plate members 55. The vertical support members 53 are adjustable in length and have one end secured to the foot platform 49. The other end of the vertical support members 53 are secured to respective support plates 55 which are secured to and extend anteriorly of the seat support frame 43.

A cross-bar member 59 is secured atop opposite sides of the frame 43 and has a bracket 57 secured thereto. The bracket 57 also extends transversely of the frame 43 and has a generally L-shaped cross-section. A pair of spaced telescopic members 61 extend anteriorly from bracket 57 to which they are secured to a location forward of seat 41. The forward ends of support members 61 are secured to respective rods 65 which are journaled in a support tube 63 which is secured by means of bracket 67 to a knee pad 60. The knee pad is nominally disposed forwardly and slightly below the seat 41. The degree to which the knee pad 60 projects forwardly of seat 41 can be varied by adjusting the extension of support 61. In addition, the knee pad is pivotable about the axis of journaled rods 65 by pivoting the support tube 63 relative to those rods.

A pair of extendible vertical supports 69 are disposed on opposite sides of seat 41 and are secured at their lower end in pivotable engagement to the seat assembly 43. The upper ends of vertical supports 69 are secured to respective journaled rods 71 which are received in a journal bearing rod 73 that is secured to the top surface of a thigh pad 70. The thigh pad is disposed above and spaced from seat 41, the spacing being determined by the extension of supports 69. The thigh pad is pivotable about the axis of journal rods 71 to accommodate the contour of a subject's thighs. The degree of extension of vertical support 69 is controlled by a hand crank 77. A similar hand crank 75 is provided for the horizontal extension control over the horizontal supports 61 for the knee pad 60.

A vertically-extending support member 79 has its lower end pivotally secured to the seat assembly frame 43 and has a sacral pad 80 secured to its upper end. Support 79 is extendible in length to adjust the height at which the sacral pad 80 resides above the seat 41. A pivot link member 85 is secured to a pivot engagement 81 at support 79 and to a pivot engagement 83 secured to frame 43. By this pivotal engagement, the support 79 can be pivoted in generally anterior and posterior directions so as to properly position the subject in the seat 41. In this regard, an alignment scale 87 is located on the left side of the subject and is formed as the distal end of a bracket secured to the sacral pad 80. The alignment scale is used in conjunction with a laser system described below for properly positioning the patient with respect to the torque transducer axis.

The sides of the subject's pelvic area are restrained by means of pads 90, 91 which act on the anterior superior iliac spines (ASIS) which pads are hereinafter referred to as the ASIS pads. The ASIS pads are positionable with three (3) degrees of freedom by means of adjustable supports 89.

The torque or moment transducer 93 is secured to bracket 93 with the axis of its input shaft 95 extending horizontally at a location above seat 41 and forward of sacral pad 80. The electrical system control box 97 is also secured to bracket 34 and is employed to control all of the electrical components in the system other than the torque transducer. Torque transducer 93, as noted above, may be the Cybex II which is commonly used for measuring the strength and endurance of human muscles. Torque transducer 93 is rigidly mounted to the mainframe 10 by means of bracket 34 secured atop the truss members 35, 37. A support table 99 is provided adjacent the structure on which are disposed the speed controllor 101 for the Cybex II torque transducer 93 and the torque recorder 103 which, for example, may be a strip chart recorder for providing a permanent output record from the torque transducer.

Figure 3:
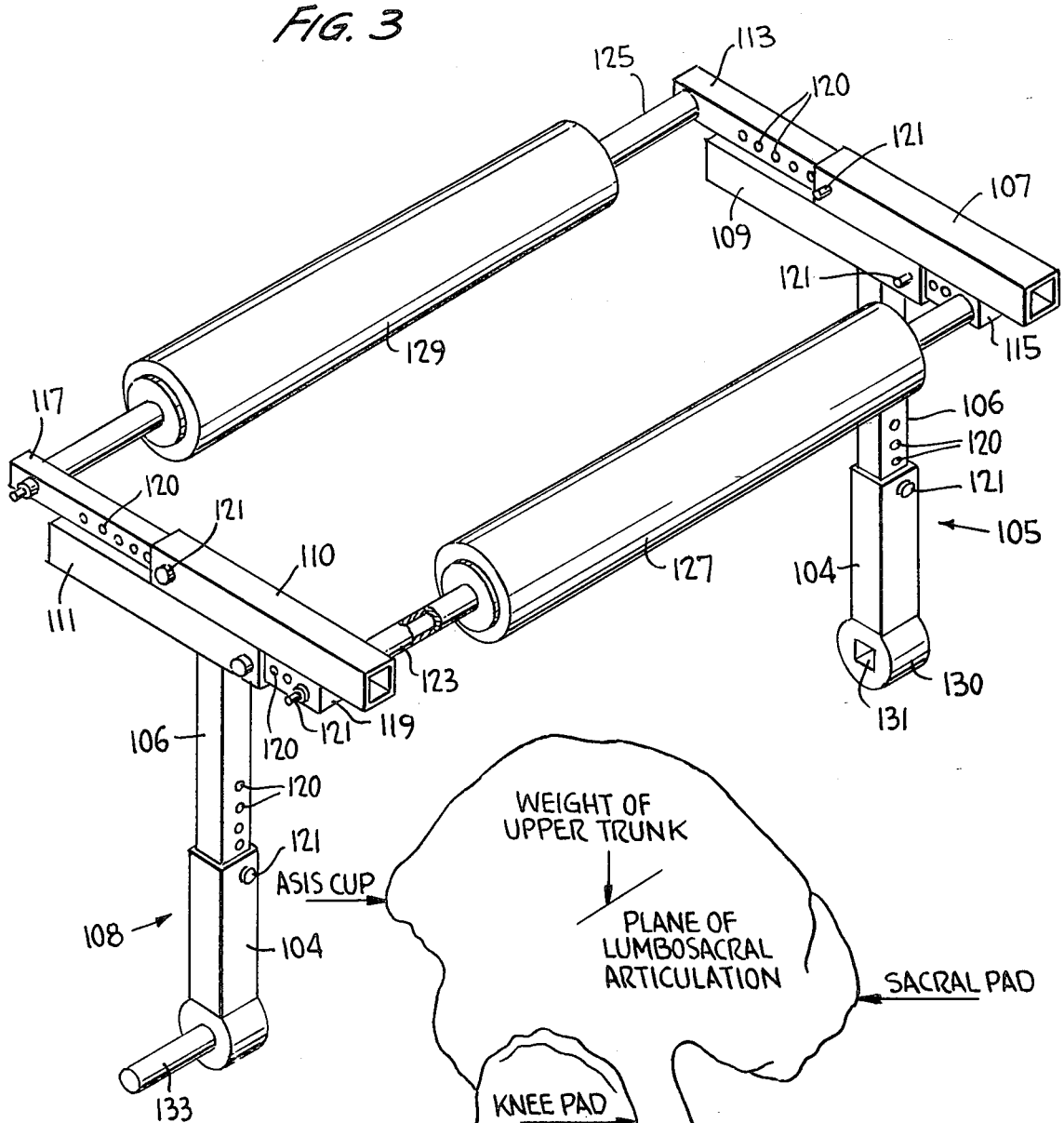
FIG. 3 is a view in perspective of the trunk pad assembly employed in the trunk dynamometer of FIGS. 1 and 2.

The trunk pad assembly, although illustrated in FIGS. 1 and 2, is more clearly illustrated in detail in FIG. 3. The torque transmission shaft 105 and a further transmission shaft 108 each include a retainer sleeve 104 of generally hollow tubular form with rectangular or square cross-section. Each retainer sleeve 104 receives a slidable bar 106 to permit the torque transmission shaft 105, 108 to be selectively extended or retracted. For this purpose, the slidable bars 106 are provided with apertures 120 extending in a longitudinal array along one side of the bar and which are selectively engaged by means of a pin 121 inserted through a suitably provided aperture in the retainer sleeve 104. Secured atop the sliding bar 106 of the torque transmission shaft 105 in perpendicular orientation thereto is a retainer sleeve 109. A similar retainer sleeve 107, extending parallel to retainer sleeve 109, is secured atop retainer sleeve 109 with its forward end projecting beyond the forward end of the sleeve 109. The rearward end of sleeve 109 projects rearwardly beyond the rearward end of sleeve 107. Sleeve 107 receives a slidable bar 113 having a plurality of apertures 120 defined therein for selective engagement by pins 121 extending through a suitably provided aperture in sleeve 107. In this manner, the projection of slidable support bar 113 from sleeve 107 can be fixed in different positions. A similar slidable support bar 115 projects forwardly from sleeve 109. A similar arrangement exists atop the slidable bar 106 for the further transmission shaft 108. Specifically, a lower retainer sleeve 111 receives a slidable bar 119 in a plurality of projecting positions. Likewise, atop retainer sleeve 107 is a further retainer sleeve 110 from which a slidable bar 117 is extendible rearwardly.

An anterior trunk pad support shaft 123 is secured between ends of slidable bars 115 and 119. A posterior trunk pad support shaft 125 is secured between ends of slidable bars 113 and 117. An elongated generally cylindrical pad is secured concentrically about shaft 123 and constitutes the anterior trunk pad 127. The posterior trunk pad 129 is similarly configured and is secured concentrically about shaft 125. The pads 127, 129 are made of medium-weight felt covered with vinyl upholstery. The anterior trunk pad 127 is offset below the posterior trunk pad 129 due to the fact that sleeves 109, 111 and their support bars 115, 119 are disposed below sleeves 107, 110, and their slidable support bars 113, 117.

The generally T-shaped support arrangement for the trunk pads 127, 129 permits the height of both pads to be adjusted simultaneously by adjusting the extension and/or retraction position of slidable bars 106 in sleeve members 104. The spacing between the pads 127 and 129 is adjustable by controlling the extension of slidable bars 113, 117 with respect to sleeves 107, 110 and the extension of bars 115, 119, with respect to sleeves 109, 111.

A connecting sleeve 130 has a generally square or rectangular aperture 131 which engages a similarly configured end of the input shaft of the torque transducer 93. In this manner, force exerted anteriorly by a subject against pad 127 or posteriorly by a subject against pad 129 is transmitted via transmission shaft 105 to apply a torque to the input shaft of the torque transducer.

The further transmission shaft 108 has an accessory shaft 133 secured to its lower end in coaxial alignment with the torque transducer input shaft 95. The accessory shaft 133, as best illustrated in FIG. 1, is secured by means of a journal bearing to the top plate 26 of the outboard truss 25, 27. The accessory shaft 133 is also employed to actuate a goniometer 135 secured to plate 30 atop the truss members 30, 31. The goniometer is employed as an indicator of the angular movement of the subject and permits the operator to instruct the subject to reverse trunk movement during a dynamic test and to identify standard positions for a static test. A counterweight 139 is suspended from the accessory shaft 133 at a location between the outboard and inboard truss members and is rigidly connected to the accessory shaft by means of a rigid support rod 138. The steel rigid support rod 138 forms a slide for the counterweight to vary the effective torque produced by the counterweight in opposition to movement of the trunk pad assembly. The counterweight is positioned such that the distance from the counterweight center of mass to the accessory shaft 133 corresponds to the position of the radius linkage of the trunk pad frame. The counterweight compensates for torque effects produced by the weight of the pads and the supporting structure so that these effects are not included in the net torque applied by the subject to the torque transducer.

A low power laser 140 is secured to the posterior horizontal support beam 13 such that it directs its low power collimated light beam upward alongside the left-hand side of the seat 41. A mirror 141 is secured to bracket 34 and positioned in the path of the beam from laser 140 so as to deflect the beam transversely across the seat assembly along the axis of rotation of input shaft 95 of the torque transducer 93. The mirror is rotatable about a point on this axis and a target 143 is provided on support plate 30 located atop truss members 29, 31 on the opposite side of the seat assembly. The mirror 141 is properly positioned when the beam from laser 140 is centered on target 143. The system and its components are illustrated in schematic inter-relationship in FIG. 4 to which reference should be made in the following discussion when the need for system perspective arises.

Figure 5:
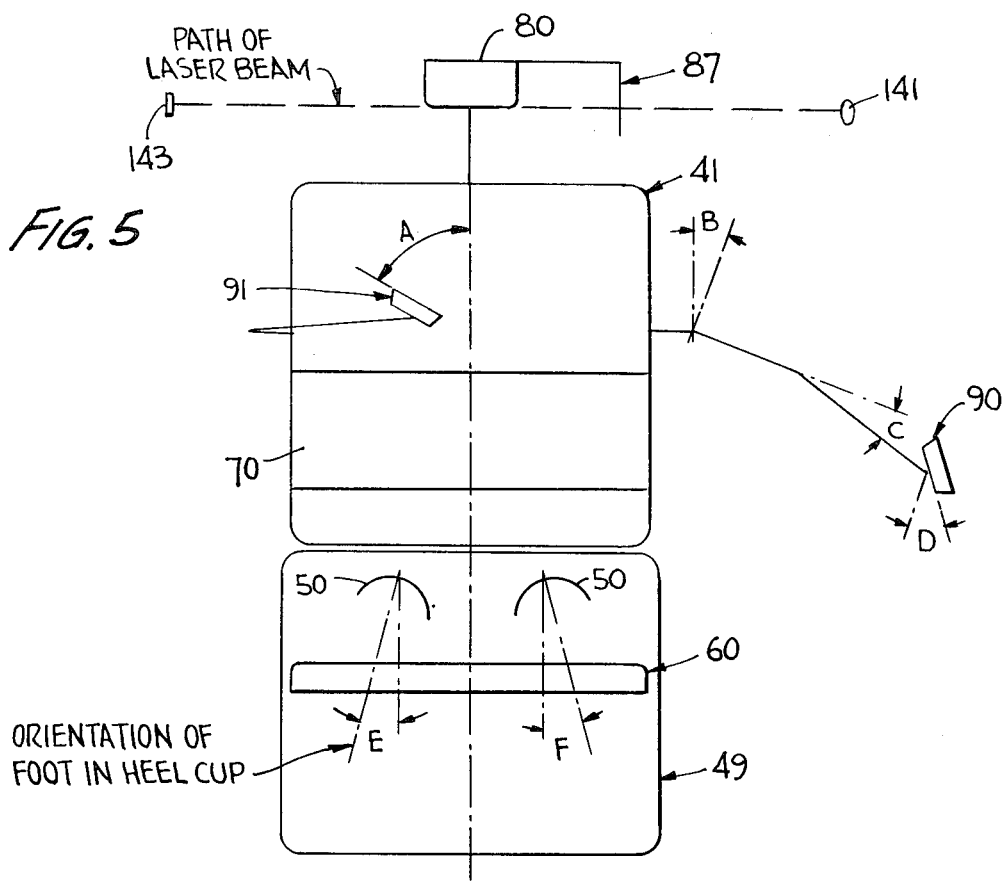
FIG. 5 is a schematic illustration from above of the stabilization, positioning, and immobilization components of the trunk dynamometer of the present invention.
Figure 6:
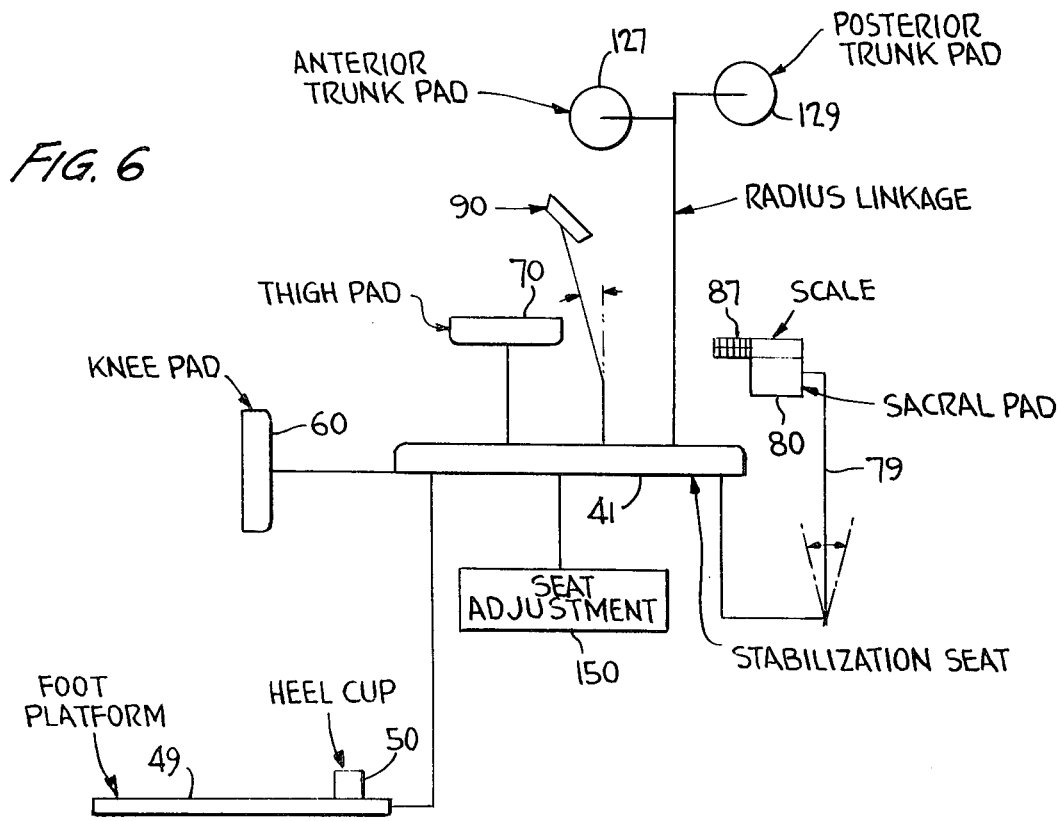
FIG. 6 is a schematic illustration from the front of the stabilization, positioning, and immobilization components of the trunk dynamometer of the present invention.

The components of the stabilization seat assembly and their relative motions are illustrated in FIGS. 5 and 6, to which specific reference is now made.

The seat 41, knee pad 60, thigh pad 70, and the sacral pad 80 are generally of wooden core construction with approximately 1.3 cm of felt padding covered by vinyl upholstery. The sacral pad 80 can be moved vertically on its support 79 which is hinged to the stabilization seat frame 43. The height of the sacral pad 80 can be incremented in steps of 1.3 cm over a range of 10.2 cm. The anteroposterior (AP) motion of the sacral pad 80 is adjustable over a continuous range of 15.2 cm.

The knee pad 60 has a continuous range of horizontal adjustability of 11.4 cm extending from 5.1 cm to 16.5 cm from the forward edge of the stabilization seat 41. The thigh pad 70 is movable vertically over a continuous range of 20.3 cm extending from a height of 5.1 cm to a height of 25.4 cm above the seat 41. The positions of the knee and thigh pads are adjusted by turning the hand cranks 75 and 77, respectively to extend and retract supports 61 and 69, respectively. The rotatability of the knee and thigh pads provide compensation for variations in the shapes of different patients.

The ASIS pads 90, 91 are bolted vertically to the sides of the stabilization seat frame 43. The bases of the pads are mounted at an acute angle B (20°) to the sides of the frame as best illustrated in FIG. 5. This configuration places the ASIS pads 90, 91 more strategically for limitation of pelvic-motion. The support structure for the pads also provides the indicated degrees of movement (as seen in FIG. 5) represented by angles A, C, and D. Angle A, which represents the horizontal angular excursion of each pad 90, 91 with respect to the anterior-posterior center line of the stabilization seat assembly, is preferably a minimum of 40° and a maximum of 60°. Angle C is preferably on the order of 17° and angle D is preferably a minimum of 20° and a maximum of 40°.

The vertical distance between the foot platform 49 and the stabilization seat 41 is adjustable in increments of 1.3 cm over a range of 17.4 cm from 34.3 cm to 52.1 cm below the seat. The construction of the foot platform is sufficient to support the weight of a human subject. The position of the subject's feet on the foot platform is established by the heel cups 50 and the Velcro straps 51 which secure the feet of the subject to the foot platform in the orientation illustrated in FIG. 5. The Velcro straps 51 are not illustrated in FIG. 5. The angles E and F represent the degree of freedom of the patient's angular orientation within the foot restraining mechanism.

In order to accommodate substantially all subjects, the stabilization seat should have a maximum vertical displacement from the axis of the torque transducer input shaft 95 on the order of 24.7 cm. This requires a range of vertical motion for the power seat mechanism on the order of 7.6 cm.

The trunk pad assembly forms a cage around the thorax of the subject. The anterior trunk pad 127 transmits spinal flexion moments to the transducer 93. The posterior trunk pad 129 transmits spinal extension moments to the transducer 93. The trunk pads are preferably 61 cm long and 8.9 cm in diameter. The compressibility of these pads is equivalent to 2.5 cm thickness of medium-weight felt. The trunk pads are covered with vinyl upholstery. The anterior trunk pad is offset below the posterior trunk pad by a distance of 3.2 cm. The trunk pads are free to rotate axially. The trunk pad frame is adjustable such that the distance between the trunk pads can be incremented in 1.3 cm steps over a 25.4 cm range. The frame also incorporates an adjustable linkage between the trunk pads and the axis of rotation of the assembly. This linkage can be incremented in length in 1.3 cm steps over a range of 17.8 cm. The radial position of this linkage defines the radial axis of the trunk pad assembly.

The accessory shaft 133 is a steel shaft having a diameter of 25.4 mm. This shaft, as described above, provides a pivot for the right side of the trunk pad frame and drives accessory apparatus in conjunction with the motion of the frame.

The counterweight 139 is preferably 16.2 kg and is adjustable along the length of rod 138 to vary the effective compensating torque provided thereby.

All of the extendible and retractable adjustable linkages for the trunk dynamometer are held in position with spring-loaded pins and compression fittings. The relative position of each linkage is preferably identified by numbers stamped along the axis of the linkage. The scale etched on the rod 138 for counterweight 139 indexes counterweight positions which produce equivalent mass distributions along the radial axis of the trunk pad assembly about the axis of rotation for torque input shaft 95. In effect, the nullifies the weight of the trunk pads and frame.

An accessory shaft lock may be provided to fix the position of the accessory shaft 133. A large cam rigidly connected to the accessory shaft can be compressed against a fixed bearing support by tightening a thumb screw.

The goniometer 135 is mounted adjacent to the radius linkage and includes a pointer attached to the lower member of the radius linkage. Goniometer 135 is scaled in 0.5° increments. A vertical orientation of the radial axis of the trunk pad assembly corresponds to 0° on the goniometer. The range of the goniometer scale is −45° to +65°.

Figure 4:
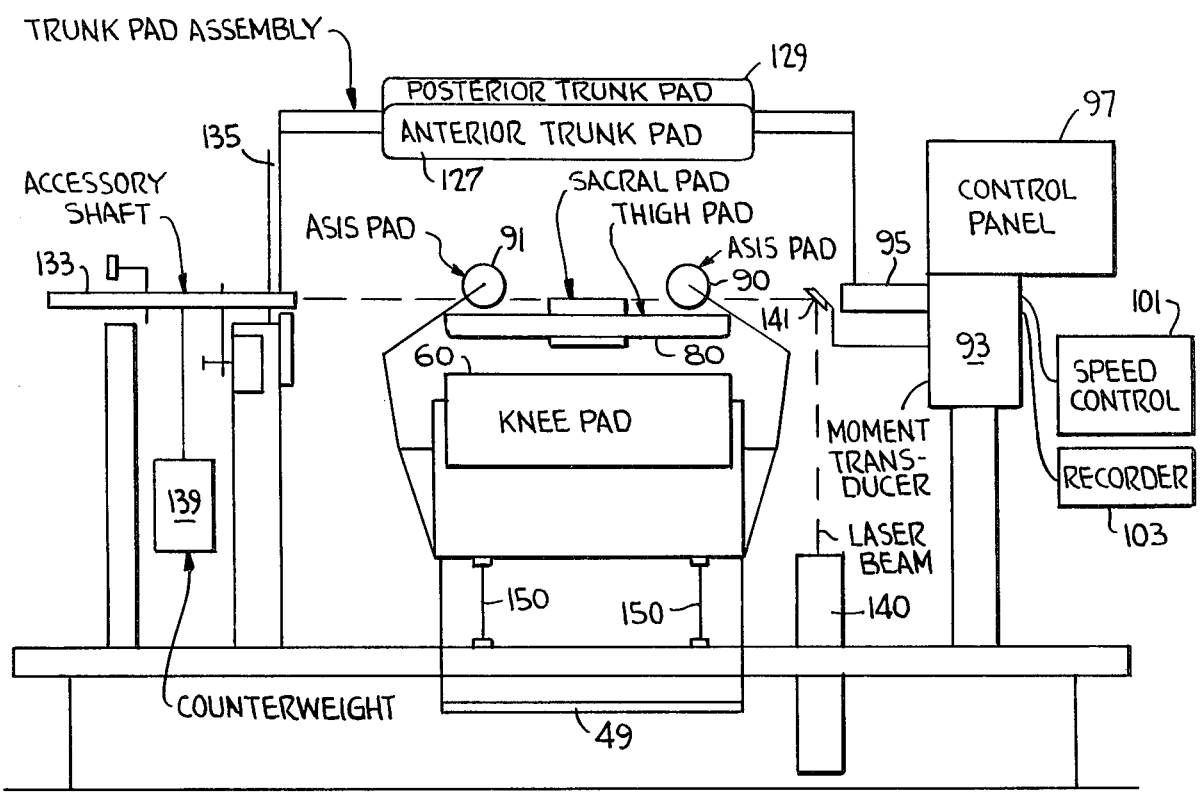
FIG. 4 is a schematic illustration of the operating components of the trunk dynamometer of FIG. 1.
Figure 7:
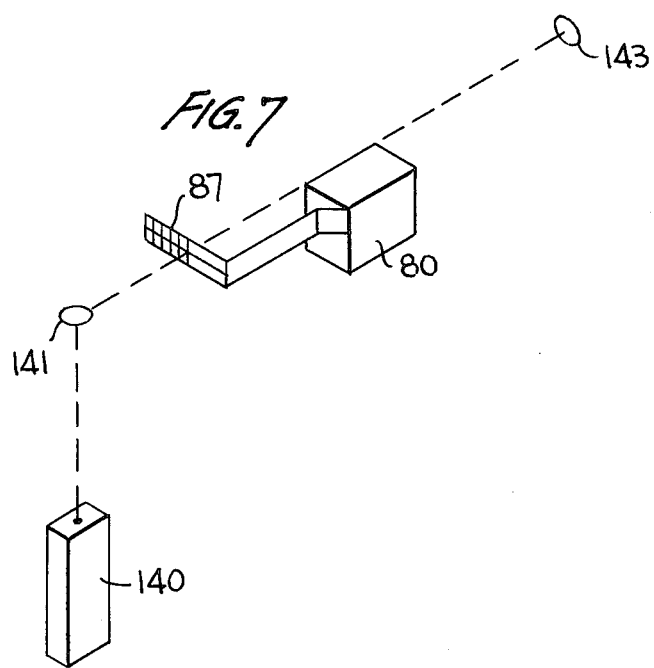
FIG. 7 is a schematic illustration of the laser alignment assembly employed for properly positioning a subject in the trunk dynamometer of the present invention.

The laser alignment system may be best understood by reference to FIGS. 7 and 4. The position of the stabilization seat with respect to the axis of rotation of the input torque shaft 95 is referenced from the applied position of the sacral pad 80. The AP positioning of the seat is referenced from the front surface of the sacral pad 80. Vertical positioning of seat 41 is referenced from the top of the sacral pad. The relative position of the stabilization seat 41 is quantified by a scale 87 attached to the back plate of the sacral pad 80. The alignment scale 87 is connected to the sacral pad so as to extend away from the area occupied by the subject. The alignment scale reads from right to left (as illustrated in FIG. 7) in centimeters from 0 to 7. The center line of the alignment scale corresponds to the height of the top of the sacral pad 80.

The low power laser 140 is reflected by mirror 141 along the axis of the torque input shaft 95 between the radius linkages of the trunk pad assembly. The alignment scale 87 serves a calibrated target for the laser beam. Operation of the power seat mechanism 150 (FIGS. 4 and 6) moves stabilization seat 41 and the alignment scale relative to the laser beam. In this way, the axis of rotation of the trunk pad assembly can be placed at specific determinable distances anterior to the sacral pad surface.

The trunk dynamometer has two (2) modes of operation, namely isometric (static) and concentric (dynamic). In the isometric mode of operation, the trunk position is controlled and the moment applied to the dynamometer by the flexors and extensors of the spine is measured. In the concentric mode of operation, the angular veocity and range of motion of the spine are controlled while the moment applied to the dynamometer by the active shortening of the flexors and extensors of the spine is measured. In both cases, analog recordings of the moment versus time are made in real time.

When a subject contracts his or her flexors or extensors of the spine, a moment is applied to the spine by these muscles. This moment tends to rotate the spine in a complex multi-segmental motion. The direction of the flexion rotation is anterior, the extension rotation is toward posterior. If the rotation of the spine is obstructed, then a force which is proportional to the spinal moment is transmitted to the obstruction. In the case of isometric flexion strength testing, the obstruction is the anterior trunk pad 127. The force applied to the anterior trunk pad 127 tends to rotate the trunk pad assembly anteriorly.

Isometric strength measurements are determined with the accessory shaft 133 locked and the transducer speed control set to 0° per second. This configuration transmits approximately half of the moment applied on the trunk pad assembly to the input shaft 95 of torque transducer 93. The relationship between the force applied to the trunk pads 127, 129 and the moment delivered to the input shaft of the transducer has been quantified in both modes of operation.

In order to complete a simple kinetic analysis of the system, one must know the line of action of the force applied to the trunk pad. With this information, the relationship between the internal moment generated by the muscles and the external moment measured by the transducer, can be quantified. In the case of concentric strength testing, the trunk pad assembly rotates about its axis (i.e., the axis of the torque input shaft 95). In theory, the transducer system provides no resistance to rotation at angular velocities which are less than the speed of the control setting. At angular velocities greater than the speed control setting, internal resistance is introduced and limits the angular velocity. The transducer system generates internal resistance in the form of a moment. The internal transducer moment is equal to the applied moment opposite in its direction. Concentric strength measurements are determined while the subject exerts a force against the moving trunk pad which is in dynamic equilibrium with the moment generated by the transducer system. The angular velocity of the trunk pad is constant because the sum of the moments acting on the trunk pad assembly is equal to 0. Angular displacement stops are employed to standardize the range of motion of the concentric strength tests. The concentric displacement from one angular displacement stop to the other constitutes one-half of a concentric exercise cycle, wherein one cycle is completed upon returning to the first displacement stop. The work done in one-half cycle (i.e., one flexion or extension excursion) is proportional to the vector product of the angular displacement and the mean magnitude of the applied moment. This is true since the mean magnitude of the moment applied to the trunk pad assembly is proportional to the mean magnitude of the force applied to the trunk pad, wherein the proportionality constant is the distance from the trunk pad to the axis of rotation (i.e., the moment arm).

The time required to complete one-half cycle is considered to be constant. This is a result of the constant velocity over a fixed displacement. Since the time is invariant, the rate of the work done (i.e., the power) in one-half cycle is dependent only on the magnitude of the moment generated. The endurance of the flexor and extensor of the spine is expressed in the time rate of moment decrement. This relationship is used as a criterion measure of the time rate of power decrement of those muscle groups. The moment decrement is the mean moment decrement across the concentric exercise cycles.

The validity of the measurements made by the trunk dynamometer depends on a number of factors. These include: the principles of muscle strength tests in general, the machanics of the trunk dynamometer, and factors that are specific to the particular mode of operation of the trunk dynamometer (that is, either isometric or concentric). These factors are discussed in general terms below.

The maximum moment that a muscle can exert on a body part is commonly used as a criterion measure for the maximum tension that the muscle can generate. This is defined as the maximum strength of the muscle which is expressed, for example, in kilograms per square centimeter of transverse section. To be meaningful, this measure must be expressed relative to the length of the muscle or the position of the body part. Several factors influence the validity of the muscle strength tests. First, the muscle or muscle group to be tested must be isolated from the muscles which may contribute a moment to the measure. In vivo this is accomplished by positioning the subject and stabilizing the subject's body parts. Next, the moment measuring device must be oriented perpendicular to the moment arm of the body part. The measurement device must also operate in the planar motion of the body part. This requires an estimate of the axis of rotation of the body part.

Strength measurements should be taken at a proportional distance from the axis of rotation of the body part when comparing measurements across subjects. This is particularly important when the force exerted by the body part is the parameter being measured. With respect to this methodology, moment measurements should also be taken at proportional distances from the axis of rotation. This is a result of the use of a relatively simple model to describe the complex kinematics of the spine.

Mechanics is only one category of factors that influence the validity of muscle strength tests. In vivo, the moment the muscle generates is subject to a volitional control. To ensure a maximal effort, the subject must be encouraged. This encouragement or stimulus must be consistent between subjects and between trials within subjects.

The trunk dynamometer of the present invention provides strength and endurance measurements of the flexors and extensors of the spine of the subject in a sitting position. In this position, the subject's hip and knees are immobilized in 90° of flexion by means of the thigh pad 70 and knee pad 60. The subject's feet are fixed in a neutral position on the foot platform 49. The subject's pelvis is prevented from rotating about the hips by means of the ASIS pads 90, 91 and the sacral pad 80. This configuration permits complete freedom of motion in the sagittal plane by the spine relative to the pelvis. Moreover, only the motion of the spine relative to the fixed pelvis is permitted. The primary advantage of this testing position is that the pelvis can be easily stabilized. Pelvic stabilization is essential to the validity of the strength measurements. If the pelvis is allowed to move relative to the femurs, then muscles that flex the hip could contribute moments to the strength measures of the spinal flexors. A similar situation exists for the muscles that extend the hip. Another advantage of this configuration is the reduced gravitational influence on the strength measurement. In general, the forces that the subject applies to the trunk pads are oriented horizontally. Gravitational acceleration cannot contribute to a force acting horizontally. The majority of the gravitational acceleration of the trunk acts only to compress the spine.

Additional support for the sitting position is the relative ease of the subject placement and removal of the test instrument. This position also places the subject's optical and vestibular apparatus in a desirable plane for spinal flexion and extension motion. The subject's head is maintained in a neutral orientation with respect to the trunk. Upper extremity position is also standardized across subjects during testing.

The purpose of the stabilization seat is three (3) fold. The primary purpose is to prevent muscles other than the spinal flexors or extensors from contributing a moment to the measurement. The second purpose is to provide a standardized reproducable body position from which spinal motion and moments can be referenced. A third purpose is to provide the subject with a firm attachment to the frame of the instrument. The necessity of this firm attachment is recognized when the large magnitude of the moments applied to the instrument is considered.

Muscles that flex and extend the trunk do not necessarily act directly on the spinal column. An objective of the trunk dynamometer is to provide strength and endurance measurements of the muscles that act directly to flex and extend the spine.

The extensors of the spine consist of a complex, serially arranged group of muscles extending from the pelvis to the skull. The most superficial group crosses the back laterally as they ascend. Excluding the muscles of the cervical spine, this group consists of the iliocostalis, longissimus, and spinalis. The deeper muscles cross the back medially as they ascend. This group consists of the semispinalis, multifidus, short rotators, and interspinalis. The intertransversiar is a deep muscle group but it does not contribute to extension. All of these muscle groups have further subdivisions, yet they act in unison to extend the spinal column.

The flexors of the spine consist of the internal and external obliques, rectus abdominus, and the psoas major and minor. Contraction of the obliques flexes the whole spinal column. The rectus flexes the lumbar region by drawing the sternum toward the pubis. The psoas minor, when present, flexes the lumbar region from the last thoracic ($T_{12}$) and first lumbar ($L_1$) vertebrae along a line to the iliopectineal eminence. The psoas major attaches to the ventral surface of all the transverse processes of the lumbar vertebrae and to the lesser tronchanter of the femur. The psoas major flexes the lumbar spine and hip.

The muscles that function primarily to flex and extend the hip also flex and extend the trunk relative to the thigh. When the thighs are immobilized as they are in the trunk dynamometer, these muscles can generate flexion or extension moments that act to move the trunk. In this case, the attachment of the hip flexors or extensors to the femur acts as the fixed origin. The attachment of these muscles to the pelvis acts as the movable insertion. When these muscles contract, a moment is applied to the pelvic which tends to rotate anteriorly or posteriorly about the hip joint. This rotation of the pelvis is transmitted to the spine. The net result is a moment which contributes to the spinal flexion or extension moment that originates from muscles not attached to the spine.

Two (2) muscles are exceptions to the foregoing description. These are the psoas major, which has attachments to both the spine and femur. The action of the psoas major is not eliminated by the stabilization system.

To mechanically prevent the hip flexor and extensor moments from influencing the spine, the position of the hip joint must be fixed. This is accomplished by fixing the position of the thighs (femurs) and the pelvis. The stabilization system immobilizes the body distal to the fifth lumbar vertebrae ($L_5$), assuming the sacroiliac joints are relatively immobile. The function of the stabilization system can be most easily understood with reference to the free body diagram of the pelvis illustrated in FIG. 8. The location of the ASIS cup or pad indexes the position of the subject in the sagittal plane relative to the stabilization seat. A center line on the seat is used as a position index in the frontal plane. Anterior and posterior displacement of the pelvis is limited by the reaction force of the sacral pad 80 against the posterior spines of the ilium of the knee pad against the posterior rim of the acetabulum, and of the ASIS pads. Inferior and superior displacement of the pelvis is limited by the reaction force of the seat against the ischial tuberosities, the weight of the trunk acting on the superior surface of the first sacral vertebrae and the thigh pad acting on the inferior rim of the acetabulum.

Flexion of the hip is limited by the reaction forces of the ASIS pad and the thigh pad. Extension of the hip is limited by the combined reaction forces of the sacral pad, knee pad, and the weight of the trunk.

The compressive force of the pads is limited by the subject tolerance. Pad composition and form is selected to high compressive forces with traumatizing overlying soft tissue.

When a force is applied to a trunk pad perpendicular to the radial axis, a moment is delivered to the input shaft at the moment transducer. This moment is equal to the vector product of the applied force and distance from the point of application of the force to the input shaft. If the applied force is not oriented perpendicular to the radial axis, only part of that force is transmitted as a moment which acts on the input shaft 95 of the torque transducer. For the purpose of this analysis, the human spine is considered to be a rigid body rotating about the moment transducer input shaft axis. The human spine is modeled as a link rotating about one end. The pivoting end represents the intervertebral space between the last lumbar ($L_5$) and the first sacral ($S_1$) vertebrae. The link represents the spinal column and the rib cage. The axis of rotation of the spine is represented by a line passing through the center of the $L_5$-$S_1$ intervertebral space perpendicular to the sagittal plane.

The validity of the moment measurement is dependent upon the spatial relationship between the axis of rotation of the measurement device and the axis of rotation of the spine. If the input shaft 95 of the moment transducer is not coaxial with the rotation of the spine, then the force applied to the trunk may not be perpendicular to the trunk pad moment arm. This situation introduces variability into the moment measurement associated with the spine position.

The axis of rotation represented by the model is aligned with the input shaft axis of rotation relative to two (2) pelvic anatomical relationships. The first, the rotation of the $L_5$-$S_1$ intervertebral space in the frontal plane, is defined as the midpoint between the posterior superior iliac spine (PSIS), and the most superior aspect of the crest of the ilium. Next, the distance from the posterior superior iliac spine to the center of the intervertebral space in the transverse plane is estimated. This estimate is established by measuring the transverse diameter of the greater pelvis of the subject and multiplying the results by a constant. The constant represents the mean ratio of the distance between the posterior superior iliac spine to the center of the $L_5$-$S_1$ intervertebral space and the transverse diameter of the greater pelvis. This mean ratio $Q_p$ is established with measurements taken from adult pelvis specimens.

To evaluate the validity of the model used to describe the motion of the spine, the predicted axis of rotation is compared with actual measurements of the motion which also give estimates of the axis of rotation. Actual measures are axes of rotation which are constructed from the displacement points on the trunk during spinal flexion and extension. Centroids are geometrically constructed points which represent the mean location of path of the instantaneous axis of rotation (centrode) of the spine. Because the spine is not a rigid body moving relative to a fixed point, the axis of rotation of the spine can be represented as a fixed body only when differentiated with respect to displacement. However, the mean location of the instantaneous axis of rotation can be specified over a particular range of motion using this method.

Another limitation of this method of analysis of spinal motion is the identification of points on the spine which do not change their planar relationship while flexion or extension is occurring. This is a result of the multi-segmental motion of the spine. The motion of an individual segment (vertebrae) is the vector sum of the motion of the spine as a whole and the local motion of the segment. The assumption is made that in the distal motion of thoracic vertebrae is not significant when compared to the motion of the spine over the range that the determination was made.

Axis of rotation data were gathered from one (1) male subject. The subject was positioned in the stabilization system with the trunk pad frame removed from the instrument. This permitted a large format camera, placed perpendicular to the sagittal plane, to have an unobstructed view of the subject's trunk. The camera was placed three (3) meters from the subject at the height of the twelfth thoracic vertebrae ($T_{12}$). The following locations were identified on the skin of the subject with grease pencil: spines of $T_{12}$, $T_4$, $C_7$, the $L_5$-$S_1$ intervertebral space, greater trochanter and the acromium. Of these landmarks, only the spine of $T_{12}$, $T_4$, and the $L_5$-$S_1$ intervertebral space and the greater trochanter were used for kinematic analysis. The subject was then photographed sitting erect (0° angular displacement position). The subject was then asked to extend his spine approximately 20° and momentarily hold this position while a photograph was taken. The procedure was repeated for 20° and 40° of flexion. Enlarge transparencies were made from the photographs. Transparencies were projected to full scale to determine the scale factor of the transparencies. The points identified on the trunk were transposed from the transparencies to tracing paper.

Spinal axes of rotation were constructed for the displacement of the $T_{12}$ and $T_4$ indices relative to the greater trochanter and the $L_5$-$S_1$ intervertebral space indices. The displacements were examined over three (3) ranges of motion of the spine. These ranges are: 40° extension to 0° (erect sitting posture), 0° to 20° flexion, and 20° flexion to 33° flexion. These angular displacements were quantified by the angle formed between the initial and final position of the index locations and the spinal axis of rotation. The spinal axis of rotation was located at the intersection of the perpendicular bisectors of lines adjoining the displaced points.

A triangle was formed on the tracing paper with vertices at the spinal axis of rotation, greater trochanter and the $L_5$-$S_1$ intervertebral space. The relationship between the transverse plane and the angle of inclination of a line connecting the greater trochanter and the $L_5$-$S_1$ intervertebral space was determined. A rectangular coordinate system was constructed with the $L_5$-$S_1$ intervertebral space represented by the origin. The greater trochanter was plotted on the coordinate system at full scale in proper relationship to the origin. The spinal axes of rotation were plotted in relationship to these points.

The location of the axis of rotation of the spine predicted by a kinematic model was also plotted. The displacement of the model axis of rotation from the spinal axis of rotation for each of the three (3) ranges was calculated. The influence of this displacement on the moment measurement was calculated for each range of angular displacement of the spine.

A subjective measurement of the ability of the stabilization seat to immobilize the pelvis and lower extremities was obtained when the transparencies were overlayed. Any change in position of the lower extremities or the greater trochanter associated with flexion and extension of the spine was beyond the resolution of visual acuity. This was true even when comparing photographs that represented the maximum measured displacement of the subject's spine (14° extension to 33° flexion). The $L_5$-$S_1$ intervertebral space tended to be displaced superiorly with flexion. This index was displaced 9 mm when the subject was flexed at 33° as compared to the position at 14° of extension. This displacement of the index was probably due primarily to motion of the skin overlying the spine. For purposes of geometric analysis, the midpoint between the displaced positions was used.

Several factors are considered when selecting the location of the trunk pad contact with the subject's trunk. In general, the trunk pads should be located at the most superior level of the spine as possible. This ensures that the moment contributions of all the extensors of the spine will be included in the measurement. The contact locations of the trunk must be capable of withstanding large compressive forces. This eliminates locations on the anterior chest wall distal to the third costal cartiliage. Large compressive forces in that region could also damage the heart or other internal organs underlying the ribs. In addition, womens' breasts oocupy that region.

The choice of site for the posterior trunk pad is less restricted. However, the scapulas provides a substantial mass that can tolerate the compressive forces.

The sitting height of the spinous process of the fourth thoracic ($T_4$) vertebrae was selected as the position index for the posterior trunk pad 129. This places the posterior trunk pad at the fifth thoracic ($T_5$) vertebrae. This also distributes the majority of the trunk pad reaction force over the scapulas.

The vertical offset of the trunk pads places the anterior trunk pad 127 in an ideal location on the anterior chest wall. The anterior trunk pad 127 is located at the height of the body of the sixth thoracic ($T_6$) vertebrae in erect sitting. This corresponds to the third costal cartilage in males. The anterior chest wall site on females tends to be relatively more cephalide, just below the sternal angle.

The anterior trunk pad height is considered ideal for several reasons. As noted above, this location is above the heart. In addition, the transverse diameter of the thorax decreases rapidly above this height. This would bring the anterior aspect of the shoulders into contact with the trunk pad. The trunk pad reaction force can be distributed over more ribs at this location on the thorax than at more superior locations. This location allows sufficient distance for the anterior trunk pad to roll up the sternum during extreme flexion without encroaching on the cranial margin of the manubrium.

Even though these pad locations are caudal to the some of the spinal extensor muscles, the thoracic spine is relatively inflexible in the range of spinal motion examined in our study. This implies that the sum of the moments acting on an individual's thoracic vertebrae is the same for all the thoracic vertebrae.

An important concern is the effect of the anterior trunk pad reaction force on pulmonary ventilation. Compensation is made for chest wall excursion when the anterior trunk pad 127 is adjusted to the AP diameter of the thorax. This is accomplished by making the distance between the trunk pads equal to the AP diameter of the subject's thorax at the end of inspiration.

Once the relative trunk pad positions are determined, the subject's trunk position can be defined by the position of the trunk pad assembly. This is true because the trunk pad assembly moves in unison with the subject's trunk. The radial axis of the trunk pad assembly is placed equidistant from the anterior and posterior chest walls. The axis of rotation of the trunk pad assembly is coaxial with the model axis of rotation of the spine. When the subject sits erect, the radial axis of the trunk pad assembly is vertical. When the radial axis is vertical, the spine position is defined to be 0°. Angular displacements of the spine are quantified by the associated angular displacement of the trunk pad assembly. Posterior (extension) angular displacements from the vertical are defined to be negative. Anterior (flexion) angular displacements from the vertical are defined to be positive.

In operating the trunk dynamometer of the present invention, the subject is seated in the stabilization seat. The posterior superior spines of ilium (PSIS) are located and the overlying skin is marked with a grease pencil. The distance between the iliac crests is measured using anthropometric calipers. Using the calipers as a guide, a mark is made on the skin over the spine indicating the height of the iliac crests. Then a ruler is used to determine the midpoint between the iliac crest mark and the level of the PSIS. This location is marked on the subject's back and is an estimate of the level of the $L_5$-$S_1$ intervertebral space. The measured distance between the iliac crests, in centimeters, is multiplied by 0.15 for female subjects and 0.20 for male subjects. The results (AP pelvis value) is recorded on a subject information form. This value determined is the sagittal plane position of the stabilization seat with respect to the transducer axis.

With the subject positioned on the center of the seat using the center line as a guide, the foot platform height is adjusted so that finger-width space is presented between the top of the seat and the toplital fossas. The anterior superior iliac spines are palpated and the ASIS pads 90, 91 are positioned directly anterior to the ASIS. The ASIS pads are locked in place and the sacral pad 80 is attached to the seat and rotated into position. The height of the sacral pad is adjusted so that the top of the pad coincides with the $L_5$ disc index. The sacral pad is compressed against the pelvis until a firm but comfortable position is obtained.

The subject's knees are positioned equidistant from the center line of the knee pad 60. The thighs are parallel and in neutral abduction. The knee pad is compressed against the tibial tuberosities until a firm but comfortable position is attained. The thigh pads 70 are rotated into position over the proximal one-third of the thighs. The thighs are compressed againt the seat by the thigh pad.

The height of the stabilization seat is adjusted to bring the center line of the alignment scale 87 to the height of the axis of rotation of the input shaft 95 of the torque transducer 93. The seat height is adjusted so that the laser beam strikes the center line of the scale 87. The seat 41 is then moved posteriorly until the distance indicated by the laser beam striking the scale is equivalent to the AP pelvis value obtained earlier. This procedure places the axis of rotation of the moment transducer in alignment with the estimate of the center of the $L_5$-$S_1$ intervertebral space.

The spinous process of the fourth thoracic ($T_4$) vertebrae is palpated and marked on the skin of the subject. The height of the trunk pad assembly is adjusted so that the center of the posterior pad is at the level of the $T_4$ spinous process. The trunk pad counterweight 139 is placed at a position corresponding to the trunk pad height.

The anterior trunk pad is placed in its guide and moved toward the subject's chest. The subject is asked to hold a moderate inspiration while the trunk pads are adjusted to the AP diameter of the chest.

The speed control unit 101 of the torque transducer 93 is adjusted to a large angular velocity to permit non-resistive motion of the subject's trunk. While the subject slowly flexes and extends the spine, all pads are observed to assure that motion is not impeded.

Isometric strength measurements are obtained in four (4) trunk positions ($-20°$, $0°$, $+20°$, and $+40°$) which are determined by the trunk pad assembly goniometer 135. In each position, the extensor strength is measured and then the flexor strength is measured. Three (3) isometric tests are conducted for each muscle group in each position.

Each strength test lasts about three (3) seconds. Following each isometric test, the speed control is momentarily increased to about 100° per second in order to relase strain in the trunk pad frame. The active range of motion in the spine is measured after the completion of isometric strength testing. This is achieved by moving the displacement stops to their end positions and requiring the subject to flex and extend as far as possible. The end points of the range of motion are measured with the goniometer and recorded.

Concentric testing is achieved with standardized spine motion range by setting the angular displacement stops at $-25°$ and $+45°$. The angular spinal velocity is standardized by setting the speed control to 30° per second.

Concentric exercise is initiated with the trunk pad frame resting against the extension displacement stop. Subjects are instructed to perform concentric exercise and until the investigator terminates the test. By observation of the first six (6) cycles, estimates of the mean peak flexion and extension moments are made. These values are halved and the results are recorded. The recorded values represent an estimate of a 50% (fifty per cent) decrement in mean peak moment. The subject continues concentric exercise until peak moment values for both flexors and extensors decrease to the estimated 50% decrement. At that limit, the subjects are instructed to relax.

From the foregoing, it will be understood that the trunk dynamometer of the present invention is a device which provides an objective measure of isometric and concentric strength and muscular endurance of the extensors and flexors of the human spine. The trunk dynamometer is adjustable for a wide range of subject body dimensions. The pelvic and lower extremity stabilization and immobilization, the subject positioning and the padded torque input arrangement are all unique to the field of muscular strength and endurance measurement.

While we have described and illustrated a specific embodiment of our invention, it will be clear that variations of the details of constructions which are specifically illustrated and described may be resorted to without departing from the true spirit and scope of the invention as defined in the appended claims.

We claim:

1. A trunk dynamometer for measuring the isometric and concentric strength and muscular endurance of a human subject's extensor and flexor muscles used in rotating the subject's trunk about an axis of spinal flexion and extension, said trunk dynamometer comprising:
   a mainframe;
   torque transducer means, including an input shaft having an axis about which said shaft is rotatable, for measuring torque applied to said input shaft about said input shaft axis, said torque transducer means being secured to said mainframe;
   a stabilization seat assembly mounted on said mainframe and including: a seat means for selectively engaging and immobilizing the pelvis, feet, thighs and knees of the subject when the subject is seated in said seat, and means for selectively moving said seat relative to said mainframe to permit substantial longitudinal alignment of said spinal axis with said shaft axis; and
   a trunk pad assembly including first and second trunk pad members and a torque transmission shaft having first and second ends, said first and second trunk pad members extending substantially horizontally in spaced relation to engage the front and back, respectively, of the subject's trunk when the subject is seated in said seat, said torque transmission shaft being secured proximate said first end to said first and second trunk pad members and proximate said second end of said input shaft of said torque transducer means to transmit torque to said input shaft as a function of the forces applied to said first and second pad members by flexion and extension of the subject's trunk about said spinal axis.

2. The trunk dynamometer according to claim 1, further comprising means for selectively adjusting the height of said first and second trunk pad members relative to the subject's trunk.

3. The trunk dynamometer according to claim 1, wherein said first and second pad members are generally cylindrical in configuration and extend parallel to one another generally transversely of the subject's spine, and wherein said trunk pad assembly further comprises an accessory shaft journaled in said mainframe and with an accessory shaft axis positioned parallel to said input shaft axis, and a further transmission shaft having first and second ends secured proximate its second end to said accessory shaft and proximate its first end to said first and second trunk pads to transmit torque from said trunk pads to said accessory shaft of said accessory shaft axis.

4. The trunk dynamometer according to claim 3, further comprising a counterweight suspended from said accessory shaft by a rigid member for applying torque to said accessory shaft in opposition to torque applied to said accessory shaft from said trunk pads through said further shaft.

5. The trunk dynamometer according to claim 1, wherein said means for selectively engaging and immobilizing the pelvis of said subject comprises:
   first and second iliac spine pads positioned on opposite sides of the subject and selectively movable relative to said seat to engage the anterior superior iliac spine of different size subjects; and
   a sacral pad, selectively movable vertically, anteriorly, and posteriorly relative to said seat to contact the sacrum of different size subjects.

6. The trunk dynamometer according to claim 5, further including alignment means comprising:
   means for directing a low power laser beam coaxially with said input shaft axis transversely across said seat; and
   a positioning scale secured to said sacral pad and extending anteriorly thereof, generally in the path of said laser beam.

7. The trunk dynamometer according to claim 6, wherein said means for selectively moving said seat includes means for selectively moving said seat up, down, anteriorly and posteriorly relative to said mainframe.

8. The trunk dynamometer according to claim 5, wherein movement of said sacral pad is effected by sacral pad adjustment means comprising:
   a substantially vertically-extending support member, extendible in length, having first and second ends;
   means securing said sacral pad to said first end of said support member;
   means securing said first end to said support member to said seat assembly for pivotal movement about a first horizontal axis;
   a pivot link member having opposite ends; and
   means pivotally securing said opposite ends to said seat assembly and said support member, respectively.

9. The trunk dynamometer according to claim 1, wherein a portion of the seat means for immobilizing the thighs of a subject comprises:
   a thigh pad having a flat padded lower surface; and
   vertically-extendible end support means secured to said opposite ends of said thigh pad and to said seat assembly for selectively raising and lowering said thigh pad relative to said seat means.

10. The trunk dynamometer according to claim 9, further comprising means for selectively pivoting said thigh pad about a horizontal axis.

11. The trunk dynamometer according to claim 10, wherein the thigh pad is a rectangular member and said bottom surface is padded and covered with a vinyl-like material.

12. The trunk dynamometer according to claim 1, wherein a portion of said seat means for immobilizing the knees of a subject comprises:
   a knee pad having a padded posterior-facing surface; and
   horizontally-extendible end support means secured to opposite ends of said knee pad and to said seat assembly to selectively extend and retract said knee pad horizontally relative to said seat means.

13. The trunk dynamometer according to claim 12, further comprising means for selectively pivoting said knee pad about a horizontal axis.

14. The trunk dynamometer according to claim 13, wherein said knee pad is a rectangular member and said posterior-facing surface is padded and covered with vinyl-like material.

15. The trunk dynamometer according to claim 1, wherein said means for selectively engaging and immobilizing the pelvis of the subject comprises:
   first and second iliac spine pads positioned on opposite sides of said seat means; and
   means for mounting said iliac spine pads to said seat assembly to permit selective movement of said spine pads relative to said seat assembly with at least three degrees of freedom of movement.

16. The trunk dynamometer according to claim 1, further comprising means for selectively adjusting the spacing between said trunk pads.

17. The trunk dynamometer according to claim 1, wherein a portion of said seat assembly for immobilizing the feet of a subject comprises a foot platform having arcuate heel restrainers secured thereto and straps for securing the feet of a subject to said platform with the subject's adjacent said heel restrainers.

18. A method for measuring the isometric and concentric strength and muscular endurance of a human subject's trunk about an axis of spinal flexion and extension, said method comprising the steps of:
   immobilizing the pelvis, feet, thighs, and knees of the subject in a seated position; and
   applying torque to the input shaft of a torque transducer as a function of force applied by a subject while flexing and extending his or her trunk about said axis.

* * * * *